United States Patent
Weissman et al.

(10) Patent No.: US 7,767,410 B2
(45) Date of Patent: Aug. 3, 2010

(54) IDENTIFICATION AND ISOLATION OF ACUTE MYELOID LEUKEMIA STEM CELLS

(75) Inventors: Irving L. Weissman, Stanford, CA (US); Naoki Hosen, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 181 days.

(21) Appl. No.: 11/999,809

(22) Filed: Dec. 7, 2007

(65) Prior Publication Data

US 2008/0187950 A1    Aug. 7, 2008

Related U.S. Application Data

(60) Provisional application No. 60/873,653, filed on Dec. 7, 2006.

(51) Int. Cl.
*C12Q 1/00* (2006.01)
*C12N 5/00* (2006.01)
*C12N 5/02* (2006.01)
*C12N 5/071* (2010.01)

(52) U.S. Cl. .................. 435/7.23; 435/4; 435/325; 435/335; 435/366; 435/372; 435/372.1

(58) Field of Classification Search ............. 435/4, 435/7.23, 325, 335, 366, 372, 372.1
See application file for complete search history.

(56) References Cited

OTHER PUBLICATIONS

Hosen et al. PNAS,104(26): 11008-11013, 2007.*
Fuchs et al. J. Immunology, 172: 3394-3398, 2004.*
Al-Hajj et al., "Prospective identification of tumorigenic breast cancer cells," Proc. Natl. Acad. Sci. USA, 2003, 100 (7):3983-3988.
Blair et al., "Lack of expression of Thy-1 (CD90) on acute myeloid leukemia cells with long-term proliferative ability in vitro and in vivo," Blood, 1997, 89(9):3104-3112.
Bonnet et al., "Human acute myeloid leukemia is organized as a hierarchy that originates from a primitive hematopoietic cell," Nat. Med., 1997, 3(7):730-737.
Jamieson et al., "Granulocyte-macrophage progenitors as candidate leukemic stem cells in blast-crisis CML," N Engl. J Med, 2004, 351(7):657-667.
Lapidot et al., "A cell initiating human acute myeloid leukaemia after transplantation into SCID mice," Nature, 1994, 367(6464):645-648.
Miyamoto et al., "AML1/ETO-expressing nonleukemic stem cells in acute myelogenous leukemia with 8;21 chromosomal translocation," Proc. Natl. Acad. Sci. USA, 2000, 97(13):7521-7526.
Pardal et al., "Applying the principles of stem-cell biology to cancer," Nat. Rev. Cancer, 2003, 3(12):895-902.
Reya et al., "Stem cells, cancer, and cancer stem cells," Nature, 2001, 414(6859):105-111.
Tan et al., "The cancer stem cell hypothesis: a work in progress," Lab. Invest., 2006, 86(12):1203-1207.
Wang et al., "Cancer stem cells: lessons from leukemia," Trends Cell Biol., 2005, 15(9):494-501.
Hope; et al., "Acute myeloid leukemia originates from a hierarchy of leukemic stem cell classes that differ in self-renewal capacity", Nature Immunology, Jul. 2004, 5(7):738-43.
Gramatzki; et al., Antibodies TC-12 (unique) and TH-111 (CD96) characterize T-ell acute lymphoblastic leukemia and a subgroup of acute myeloid leukemia, Exp. Hematol (1998), 26:1209-1214.
Repp; et al., "Immunophenotyping is an independent factor for risk stratification in AML", Cytometry (2003), 53B (1):11-19.

\* cited by examiner

*Primary Examiner*—Thaian N Ton
(74) *Attorney, Agent, or Firm*—Bozicevic, Field & Francis LLP; Pamela J. Sherwood (57) ABSTRACT

Acute myeloid leukemia stem cells (AMLSC) are identified. The cells can be prospectively isolated or identified from patient samples, and are shown to possess the unique properties of cancer stem cells in functional assays for cancer stem cell self-renewal and differentiation, and in cancer diagnosis.

6 Claims, 4 Drawing Sheets
(1 of 4 Drawing Sheet(s) Filed in Color)

Fig.1 CD96 expression in AML. (A-C) representative staining profiles of AML samples with CD96, CD34, CD38, and CD90. (D) The percentages of CD96+ cells in CD34+CD38- populations of each AML samples. The expression in normal BM CD34+CD38- cells, which contains bith of CD90+ and CD90- fractions, are shown for comparison.

Fig.2 CD96 expression in normal BM cells. G8.5 or TH-111 is the name of the antibody clone. Note that there are almost no CD96+ cells in the normal HSC (CD34+CD38-Lin-CD90+) cells.

Fig.3 CD96+ AML cells are enriched with LSCs. AML cells were separated into CD96+ and CD96- cells and transplanted into irradiated (100cGy) new-born Rag2/common γ chain double knock-out mice. The chimerisms of human cells (hCD45+ cells) in peripheral blood (PB) at 4week, and in bone marrow (BM) and spleen (Sp) at 10 weeks are shown. Each dot corresponds to a recipient. Two mice that had high chimerism of human cells at 4 weeks died of spreading leukemia before the analsyis at 10week. In Pt.4, both of CD96+ and CD96- populations could engraft extensively.

Fig 4 CD96 is a marker of AML-LSC. (A, D, G) Representative results of tranaplantation of CD96+ or CD96- AML cells. The FACS profiles and sorting gates are shown in the left. The chimerism of human cells in peripheral blood (PB), bone marrow (BM), and Spleen (Sp) were analyzed at 10 weeks post rtranplant. (B, E, H) engrafted leukemia cells still contained CD96+ fraction. (C, F, I) M-G staining of the PB of engrafted mice, showing that engrafted human CD45+ cells are leukemia cells

IDENTIFICATION AND ISOLATION OF ACUTE MYELOID LEUKEMIA STEM CELLS

FEDERALLY-SPONSORED RESEARCH OR DEVELOPMENT

This invention was made with Government support under contract CA086017 awarded by the National Cancer Institute. The Government has certain rights in this invention.

BACKGROUND OF THE INVENTION

Basic cancer research has focused on identifying the genetic changes that lead to cancer. This has led to major advances in our understanding of the molecular and biochemical pathways that are involved in tumorigenesis and malignant transformation. However, our understanding of the cellular biology has lagged. Although the effects of particular mutations on the proliferation and survival of model cells, such as fibroblasts or cell lines, can be predicted, the effects of such mutations on the actual cells involved in specific cancers is largely guesswork.

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop. Many observations suggest that analogies between normal stem cells and tumorigenic cells are appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials.

Because most tumors have a clonal origin, the original tumorigenic cancer cell gives rise to phenotypically diverse progeny, including cancer cells with indefinite proliferative potential, as well as cancer cells with limited or no proliferative potential. This suggests that tumorigenic cancer cells undergo processes that are analogous to the self-renewal and differentiation of normal stem cells. Tumorigenic cells can be thought of as cancer stem cells that undergo an aberrant and poorly regulated process of organogenesis analogous to what normal stem cells do. Although some of the heterogeneity in tumors arises as a result of continuing mutagenesis, it is likely that heterogeneity also arises through the aberrant differentiation of cancer cells.

It is well documented that many types of tumors contain cancer cells with heterogeneous phenotypes, reflecting aspects of the differentiation that normally occurs in the tissues from which the tumors arise. The variable expression of normal differentiation markers by cancer cells in a tumor suggests that some of the heterogeneity in tumors arises as a result of the anomalous differentiation of tumor cells. Examples of this include the variable expression of myeloid markers in chronic myeloid leukaemia, the variable expression of neuronal markers within peripheral neurectodermal tumors, and the variable expression of milk proteins or the estrogen receptor within breast cancer.

It was first extensively documented for leukemia and multiple myeloma that only a small subset of cancer cells is capable of extensive proliferation. Because the differences in clonogenicity among the leukemia cells mirrored the differences in clonogenicity among normal hematopoietic cells, the clonogenic leukemic cells were described as leukemic stem cells. It has also been shown for solid cancers that the cells are phenotypically heterogeneous and that only a small proportion of cells are clonogenic in culture and in vivo. Just as in the context of leukemic stem cells, these observations led to the hypothesis that only a few cancer cells are actually tumorigenic and that these tumorigenic cells act as cancer stem cells.

In support of this hypothesis, recent studies have shown that, similar to leukemia and other hematologic malignancies, tumorigenic and non-tumorigenic populations of breast cancer cells can be isolated based on their expression of cell surface markers. In many cases of breast cancer, only a small subpopulation of cells had the ability to form new tumors. This work strongly supports the existence of CSC in breast cancer. Further evidence for the existence of cancer stem cells occurring in solid tumors has been found in central nervous system (CNS) malignancies. Using culture techniques similar to those used to culture normal neuronal stem cells it has been shown that neuronal CNS malignancies contain a small population of cancer cells that are clonogenic in vitro and initiate tumors in vivo, while the remaining cells in the tumor do not have these properties.

Stem cells are defined as cells that have the ability to perpetuate themselves through self-renewal and to generate mature cells of a particular tissue through differentiation. In most tissues, stem cells are rare. As a result, stem cells must be identified prospectively and purified carefully in order to study their properties. Perhaps the most important and useful property of stem cells is that of self-renewal. Through this property, striking parallels can be found between stem cells and cancer cells: tumors may often originate from the transformation of normal stem cells, similar signaling pathways may regulate self-renewal in stem cells and cancer cells, and cancers may comprise rare cells with indefinite potential for self-renewal that drive tumorigenesis.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that immune surveillance is highly effective at killing disseminated cancer cells before they can form a detectable tumor. Another possibility is that most cancer cells lack the ability to form a new tumor such, that only the dissemination of rare cancer stem cells can lead to metastatic disease. If so, the goal of therapy must be to identify and kill this cancer stem cell population.

The prospective identification and isolation of cancer stem cells will allow more efficient identification of diagnostic markers and therapeutic targets expressed by the stem cells. Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

Cancer stem cells are discussed in, for example, Pardal et al. (2003) Nat Rev Cancer 3, 895-902; Reya et al. (2001) Nature 414, 105-11; Bonnet & Dick (1997) Nat Med 3, 730-7; Al-Hajj et al. (2003) Proc Natl Acad Sci U S A 100, 3983-8; Dontu et al. (2004) Breast Cancer Res 6, R605-15; Singh et al. (2004) Nature 432, 396-401.

SUMMARY OF THE INVENTION

Acute myeloid leukemia stem cells (AMLSC) are identified herein. The cells can be prospectively isolated or identified from primary tumor samples, and are shown to possess the unique properties of cancer stem cells in functional assays for cancer stem cell self-renewal and differentiation, and to form unique histological features useful in cancer diagnosis. The AMLSC have the phenotype of being positive for expression of CD96.

In some embodiments of the invention, methods are provided for detection, classification or clinical staging of acute myeloid leukemias according to the stem cells that are present in the leukemia, where greater numbers of stem cells are indicative of a more aggressive cancer phenotype. Staging is useful for prognosis and treatment. In some embodiments, a tumor sample is analyzed by histochemistry, including immunohistochemistry, in situ hybridization, and the like, for the presence of $CD34^+CD38^-$ cells that express CD96. The presence of such cells indicates the presence of AMLSC.

In another embodiment of the invention, compositions of isolated AMLSC are provided. The cells are useful for experimental evaluation, and as a source of lineage and cell specific products, including mRNA species useful in identifying genes specifically expressed in these cells, and as targets for the discovery of factors or molecules that can affect them. AMLSC may be used, for example, in a method of screening a compound for an effect on the cells. This involves combining the compound with the cell population of the invention, and then determining any modulatory effect resulting from the compound. This may include examination of the cells for viability, toxicity, metabolic change, or an effect on cell function. The phenotype of AMLSC described herein provides a means of predicting disease progression, relapse, and development of drug resistance.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Acute myeloid leukemias are staged by analysis of the presence of cancer stem cells. Staging is useful for prognosis and treatment. In one embodiment of the invention, a sample from an acute myeloid leukemia patient is stained with reagents specific for CD96; and optionally with CD34 and CD38. The analysis of staining patterns provides the relative distribution of AMLSC, which distribution predicts the stage of leukemia. In some embodiments, the sample is analyzed by histochemistry, including immunohistochemistry, in situ hybridization, and the like, for the presence of $CD34^+CD38^-$ cells that express CD96. The presence of such cells indicates the presence of AMLSC.

In one embodiment, the patient sample is compared to a control, or a standard test value. In another embodiment, the patient sample is compared to a pre-leukemia sample, or to one or more time points through the course of the disease.

Samples, including tissue sections, slides, etc. containing an acute myeloid leukemia tissue; are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the leukemia.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

In some embodiments of the invention, the number of $CD96^+$ AML cancer cells in a patient sample is determined relative to the total number of AML cancer cells, where a greater percentage of $CD96^+$ cells is indicative of the presence of cancer stem cells, and the potential for continued self-renewal of cells with the cancer phenotype. The total AML cancer cells may be approximately quantited by quantitating blast cells in the blood. The quantitation of $CD96^+$ cells in a patient sample may be compared to a reference population, e.g. a patient sample such as a blood sample, a remission patient sample, etc. In some embodiments, the quantitation of CD96+ cells is performed during the course of treatment, where the number of AML cancer cells and the percentage of such cells that are AMLSC are quantitated before, during and as follow-up to a course of therapy. Desirably, therapy targeted to cancer stem cells results in a decrease in the total number, and/or percentage of AMLSC in a patient sample.

In other embodiments of the invention, anti-cancer agents are targeted to AMLSC by specific binding to CD96. In such embodiments, the anti-cancer agents include antibodies and antigen-binding derivatives thereof specific for CD96, which are optionally conjugated to a cytotoxic moiety. Depletion of AMLSC is useful in the treatment of AML. Depletion achieves a reduction in circulating AMLSC by up to about 30%, or up to about 40%, or up to about 50%, or up to about 75% or more. Depletion can be achieved by using a CD96-binding agent to deplete AMLSC either in vivo or ex vivo.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

As summarized above, the subject invention is directed to methods of classification of cancers, as well as reagents and kits for use in practicing the subject methods. The methods may also determine an appropriate level of treatment for a particular cancer.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research of acute myeloid leukemias. Acute leukemias are rapidly progressing leukemia characterized by replacement of normal bone marrow by blast cells of a clone arising from malignant transformation of a hematopoietic stem cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas). AML is the most common acute leukemia affecting adults, and its incidence increases with age. While AML is a relatively rare disease overall, accounting for approximately 1.2% of cancer deaths in the United States, its incidence is expected to increase as the population ages.

The presenting symptoms are usually nonspecific (e.g., fatigue, fever, malaise, weight loss) and reflect the failure of normal hematopoiesis. Anemia and thrombocytopenia are very common (75 to 90%). The WBC count may be decreased, normal, or increased. Blast cells are usually found in the blood smear unless the WBC count is markedly decreased. The blasts of ALL can be distinguished from those of AML by histochemical studies, cytogenetics, immunophenotyping, and molecular biology studies. In addition to smears with the usual stains, terminal transferase, myeloperoxidase, Sudan black B, and specific and nonspecific esterase.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

As used throughout, "modulation" is meant to refer to an increase or a decrease in the indicated phenomenon (e.g., modulation of a biological activity refers to an increase in a biological activity or a decrease in a biological activity).

Characterization of Acute Myeloid Leukemia Stem Cells

In acute myeloid leukemias, characterization of cancer stem cells allows for the development of new treatments that are specifically targeted against this critical population of cells, particularly their ability to self-renew, resulting in more effective therapies.

In human acute myeloid leukemias it is shown herein that there is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. Tumorigenic potential was contained within the CD96+ subpopulation of cancer cells.

In some embodiments of the invention, the number of $CD96^+$ AML cancer cells in a patient sample is determined relative to the total number of AML cancer cells, where a greater percentage of $CD96^+$ cells is indicative of the presence of cancer stem cells, and the potential for continued self-renewal of cells with the cancer phenotype. The quantitation of $CD96^+$ cells in a patient sample may be compared to a reference population, e.g. a patient sample such as a blood sample, a remission patient sample, etc. In some embodiments, the quantitation of CD96+ cells is performed during the course of treatment, where the number of AML cancer cells and the percentage of such cells that are AMLSC are quantitated before, during and as follow-up to a course of therapy. Desirably, therapy targeted to cancer stem cells results in a decrease in the total number, and/or percentage of AMLSC in a patient sample.

In other embodiments of the invention, anti-cancer agents are targeted to AMLSC by specific binding to CD96. In such embodiments, the anti-cancer agents include antibodies and antigen-binding derivatives thereof specific for CD96, which are optionally conjugated to a cytotoxic moiety. Depletion of AMLSC is useful in the treatment of AML. Depletion achieves a reduction in circulating AMLSC by up to about 30%, or up to about 40%, or up to about 50%, or up to about 75% or more. Depletion can be achieved by using a CD96-binding agent to deplete AMLSC either in vivo or ex vivo.

The AMLSC are identified by their phenotype with respect to particular markers, and/or by their functional phenotype. In some embodiments, the AMLSC are identified and/or isolated by binding to the cell with reagents specific for the markers of interest. The cells to be analyzed may be viable cells, or may be fixed or embedded cells.

In some embodiments, the reagents specific for the markers of interest are antibodies, which may be directly or indirectly labeled. Such antibodies will usually include antibodies specific for CD96.

Acute Myeloid Leukemia

Acute Myelocytic Leukemia (AML, Acute Myelogenous Leukemia; Acute Myeloid Leukemia). In AML, malignant transformation and uncontrolled proliferation of an abnormally differentiated, long-lived myeloid progenitor cell results in high circulating numbers of immature blood forms and replacement of normal marrow by malignant cells. Symptoms include fatigue, pallor, easy bruising and bleeding, fever, and infection; symptoms of leukemic infiltration are present in only about 5% of patients (often as skin manifestations). Examination of peripheral blood smear and bone marrow is diagnostic. Treatment includes induction chemotherapy to achieve remission and post-remission chemotherapy (with or without stem cell transplantation) to avoid relapse.

AML has a number of subtypes that are distinguished from each other by morphology, immunophenotype, and cytochemistry. Five classes are described, based on predominant cell type, including myeloid, myeloid-monocytic, monocytic, erythroid, and megakaryocytic. Acute promyelocytic leukemia is a particularly important subtype, representing 10 to 15% of all cases of AML, striking a younger age group (median age 31 yr) and particular ethnicity (Hispanics), in which the patient commonly presents with a coagulation disorder.

Remission induction rates range from 50 to 85%. Long-term disease-free survival reportedly occurs in 20 to 40% of patients and increases to 40 to 50% in younger patients treated with stem cell transplantation.

Prognostic factors help determine treatment protocol and intensity; patients with strongly negative prognostic features are usually given more intense forms of therapy, because the potential benefits are thought to justify the increased treatment toxicity. The most important prognostic factor is the leukemia cell karyotype; unfavorable karyotypes include t(15; 17), t(8; 21), and inv16 (p13; q22). Other negative factors include increasing age, a preceding myelodysplastic phase, secondary leukemia, high WBC count, and absence of Auer rods. The FAB or WHO classification alone does not predict response.

Initial therapy attempts to induce remission and differs most from ALL in that AML responds to fewer drugs. The basic induction regimen includes cytarabine by continuous IV infusion or high doses for 5 to 7 days; daunorubicin or idarubicin is given IV for 3 days during this time. Some regimens include 6-thioguanine, etoposide, vincristine, and prednisone, but their contribution is unclear. Treatment usually results in significant myelosuppression, with infection or bleeding; there is significant latency before marrow recovery. During this time, meticulous preventive and supportive care is vital.

Differential Cell Analysis

The presence of AMLSC in a patient sample can be indicative of the stage of the leukemia. In addition, detection of AMLSC can be used to monitor response to therapy and to aid in prognosis. The presence of AMLSC can be determined by quantitating the cells having the phenotype of the stem cell. In addition to cell surface phenotyping, it may be useful to quantitate the cells in a sample that have a "stem cell" character, which may be determined by functional criteria, such as the ability to self-renew, to give rise to tumors in vivo, e.g. in a xenograft model, and the like.

Clinical samples for use in the methods of the invention may be obtained from a variety of sources, particularly blood, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cell staining will use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described.

The comparison of a differential progenitor analysis obtained from a patient sample, and a reference differential progenitor analysis is accomplished, by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

AMLSC Compositions

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for AMLSC are achieved in this manner. The subject population may be at or about 50% or more of the cell composition, and preferably be at or about 75% or more of the cell composition, and may be 90% or more. The desired cells are identified by their surface phenotype, by the ability to self-renew, ability to form tumors, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for AMLSC may be used in a variety of screening assays and cultures, as described below.

The enriched AMLSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3: 213-235) or "Dexter" culture conditions (Dexter et al. [1977] *J Exp Med* 145: 1612-1616); and heterogeneous thymic stromal Screening Assays AMLSC are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, antiproliferative drugs, etc. the AMLSC composition, usually a culture comprising AMLSC, is contacted with the agent of interest, and the effect of the agent assessed by monitoring output parameters, such as expression of markers, cell viability, and the like. The cells may be freshly isolated, cultured, genetically altered, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, New York, (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12): 477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1): 112-225; Kawamoto et al. (1999) *Genome Res* 9(12): 1305-12; and Chen et al. (1998) *Genomics* 51(3): 313-24, for examples.

Depletion of AMLSC

Depletion of AMLSC is useful in the treatment of AML. Depletion can be achieved by several methods. Depletion is defined as a reduction in the target population by up to about 30%, or up to about 40%, or up to about 50%, or up to about 75% or more. An effective depletion is usually determined by the sensitivity of the particular disease condition to the levels of the target population. Thus in the treatment of certain conditions a depletion of even about 20% could be beneficial.

A CD96-specific agent that specifically depletes the targeted AMLSC is used to contact the patient blood in vitro or in vivo, wherein after the contacting step, there is a reduction in the number of viable AMLSC in the targeted population. An exemplary agent for such purposes is an antibody that specifically binds to CD96 on the surface of the targeted AMLSC. An effective dose of antibodies for such a purpose is sufficient to decrease the targeted population to the desired level, for example as described above. Antibodies for such purposes may have low antigenicity in humans or may be humanized antibodies.

In one embodiment of the invention, antibodies for depleting target population are added to patient blood in vivo. In another embodiment, the antibodies are added to the patient blood ex vivo. Beads coated with the antibody of interest can be added to the blood, target cells bound to these beads can then be removed from the blood using procedures common in the art. In one embodiment the beads are magnetic and are removed using a magnet. Alternatively, when the antibody is biotinylated, it is also possible to indirectly immobilize the antibody onto a solid phase which has adsorbed avidin, streptavidin, or the like. The solid phase, usually agarose or sepharose beads are separated from the blood by brief centrifugation. Multiple methods for tagging antibodies and removing such antibodies and any cells bound to the antibodies are routine in the art. Once the desired degree of depletion has been achieved, the blood is returned to the patient. Depletion of target cells ex vivo decreases the side effects such as infusion reactions associated with the intravenous administration. An additional advantage is that the repertoire of available antibodies is expanded significantly as this procedure does not have to be limited to antibodies with low antigenicity in humans or humanized antibodies.

Kits may be provided, where the kit will comprise staining reagents that are sufficient to differentially identify the AMLSC described herein. A marker combination of interest may include CD96, CD34, and CD38. The staining reagents are preferably antibodies, and may be detectably labeled. Kits may also include tubes, buffers, etc., and instructions for use.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Experimental

Treatment of acute myeloid leukemia (AML) is difficult, because most drugs do not target leukemic stem cells (LSC), which can self-renew and propagate leukemia progeny. One of the most promising ways to target LSC is antibody therapy, which has been successful in many types of malignancies. It is very important to identify antigens that express specifically in leukemia stem cells but not in normal hematopoietic stem cells (HSC) as the first step for developing LSC-targeting antibody therapy.

To identify LSC-specific antigen, we first cloned many cell surface molecules expressed on $CD34^+CD38^-$ population, which has been reported to be enriched with LSCs, in a AML patient, using signal sequence trap PCR method. Then, we chose the candidates for AML-LSC antigen from the list of the cloned molecules and examined their expression in AML-LSC populations ($CD34^+CD38^-$) in several different AML samples and HSC populations ($CD34^+CD38^-Lin^-$) in normal bone marrow, (BM) cells by quantitative RT-PCR. As a result, we found that CD96 is expressed at very high levels in LSC populations, but very low in normal HSC populations.

Figure 1:
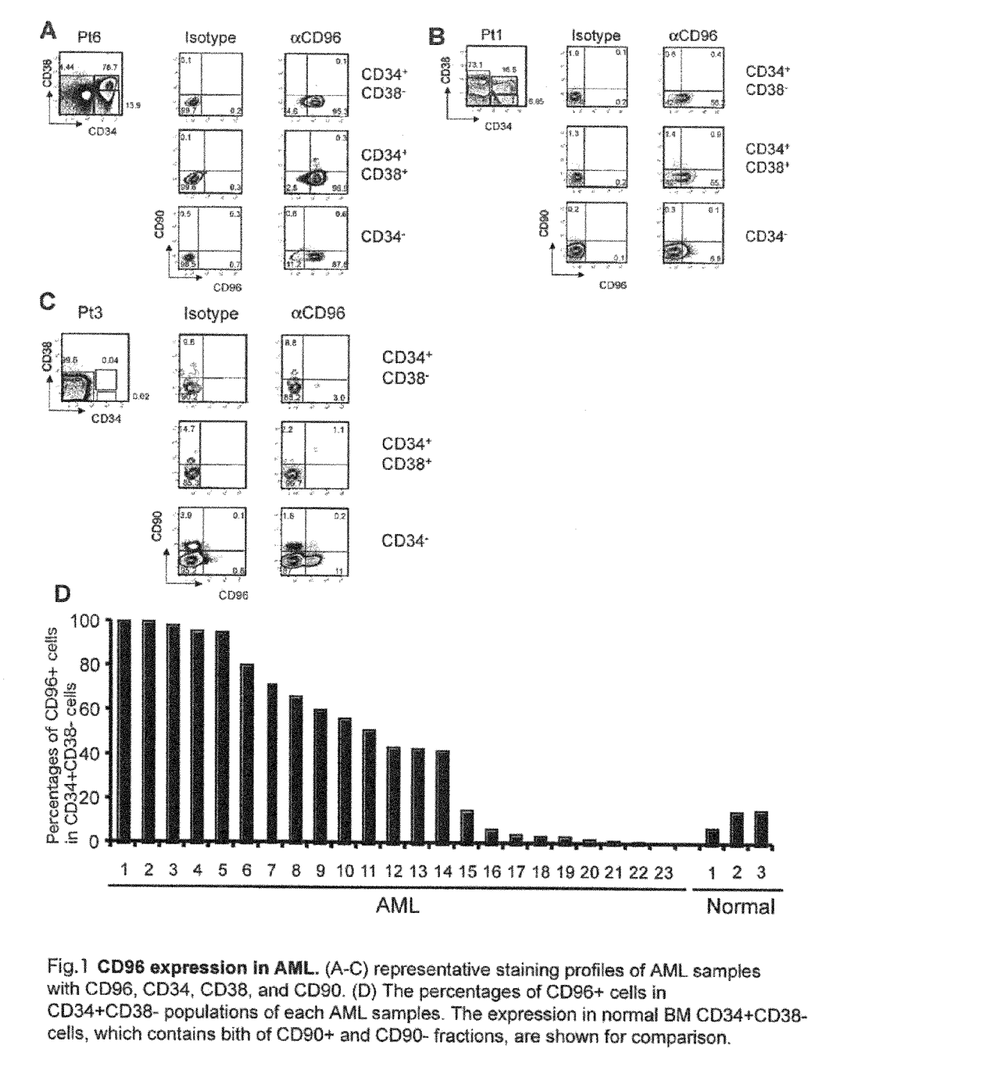
FIG. 1. CD96 expression in AML. (A-C) representative staining profiles of AML samples with CD96, CD34, CD38, and CD90. (D) The percentages of CD96+ cells in CD34+ CD38− populations of each AML samples. The expression in normal BM CD34+CD38− cells, which contains both CD90+ and CD90− fractions, are shown for comparison.
Figure 2:
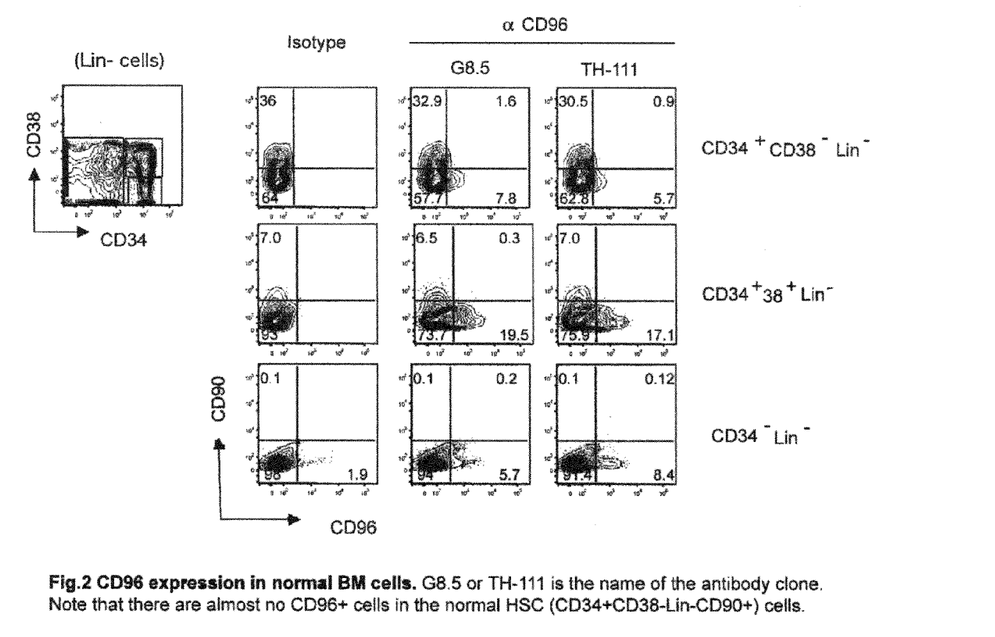
FIG. 2. CD96 expression in normal BM cells. G8.5 or TH-111 is the name of the antibody clone. Note that there are almost no CD96+ cells in the normal HSC (CD34+CD38− Lin-CD90+) cells.
Figure 3:
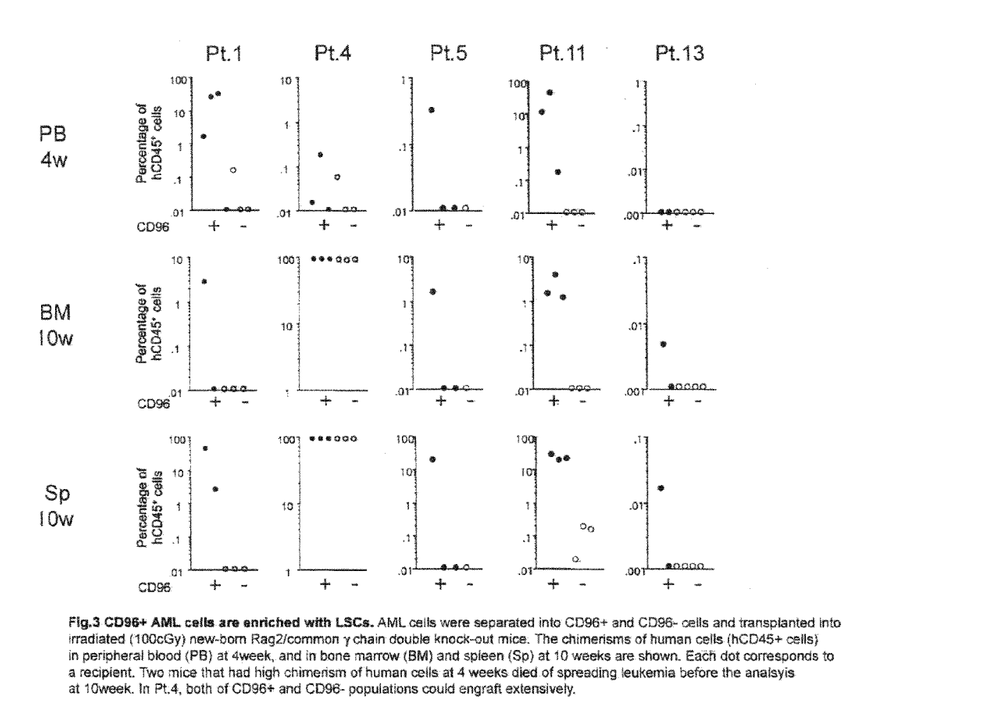
FIG. 3. AML cells are enriched with LSCs. AML cells were separated into CD96+ and CD96− cells and transplanted into irradiated (100 cGy) new-born Rag2 common γ chain double knock-out mice. The chimerisms of human cells (hCD45+ cells) in peripheral blood (PB) at 4 weeks, and in bone marrow (BM) and spleen (Sp) at 10 weeks are shown. Each dot corresponds to a recipient. Two mice that had high chimerism of human cells at 4 weeks died of spreading leukemia before the analysis at 10 weeks. In Pt.4, both of CD96+ and CD96− populations could engraft extensively.
Figure 4:
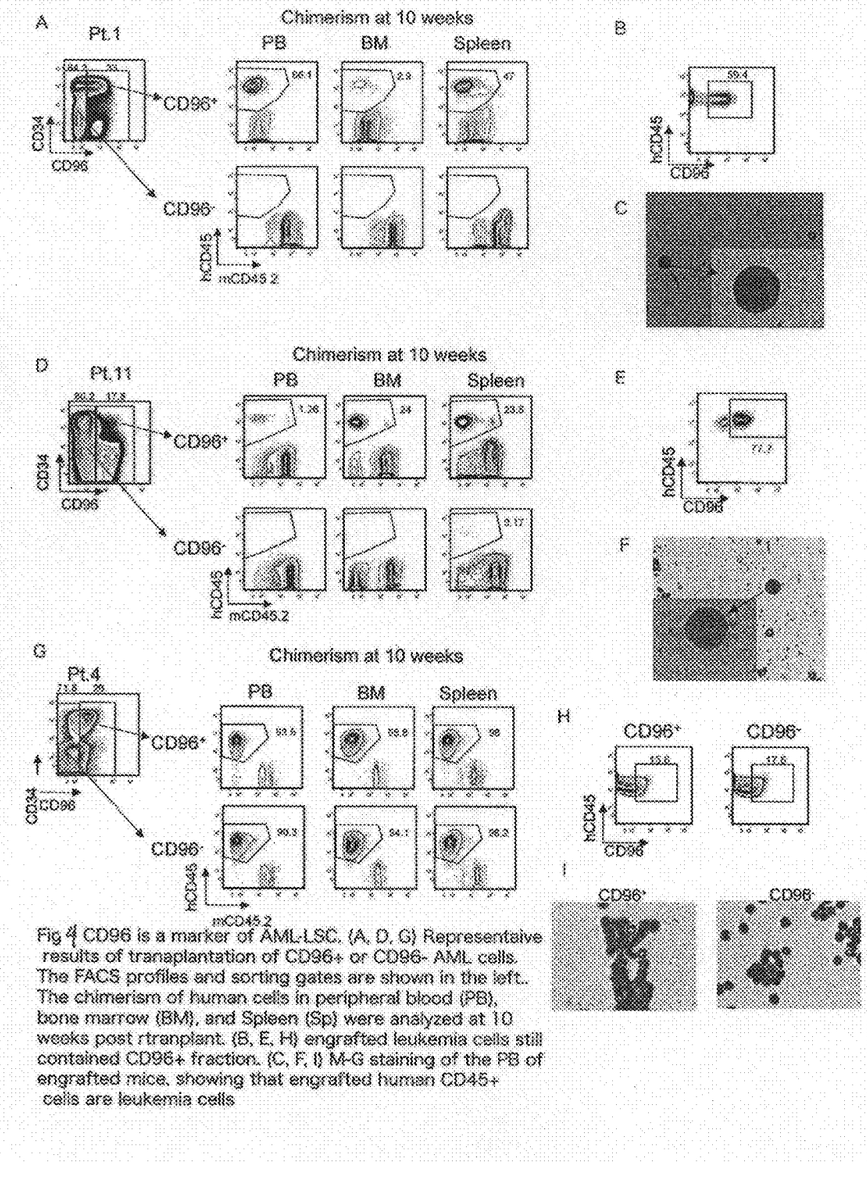
FIG. 4. CD96 is a marker of AML-LSC. (A, D, G) Representative results of transplantation of CD96+ or CD96− AML cells. The FACS profiles and sorting gates are shown in the left. The chimerism of human cells (hCD45+) in peripheral blood (PB), bone marrow (BM), and spleen (Sp) were analyzed at 10 weeks post transplant. (B, E, H) Engrafted leukemia cells still contained CD96+ fraction. (C, F, I) M-G staining of the PB of engrafted mice, showing that engrafted human CD45+ cells are leukemia cells.

To confirm this finding, we stained many AML samples with anti-CD96 antibody and found that the majority (71.5±21.9%) of AML $CD34^+CD38^-$ cells expressed CD96 in many cases (14/23: 61%) (FIG. 1), while normal HSC ($Lin^- CD34^+CD38^-CD90^+$) never express it (FIG. 2). Finally, we examine whether $CD96^+$ AML cells is enriched with LSCs, we perform functional analysis by transplanting them to immuno-deficient mice. We separated AML cells into $CD96^+$ and $CD96^-$ fractions by FACS-sorting and transplanted into irradiated (100 cGy) new-born Rag2/common γ chain double knock-out mice. In 4 of 5 cases, only $CD96^+$ fraction could show significant engraftment to the recipients at least for 10 weeks, while both of $CD96^+$ and $CD96^-$ population engrafted in one samples (FIG. 3).

These results demonstrate that CD96 is expressed on LSCs in the majority of AMLs, but not on normal HSCs, indicating that CD96 is a novel therapeutic target against AML-LSCs.

What is claimed is:

1. A method for staging acute myeloid leukemia (AML) from a patient suffering from AML, the method comprising:
   isolating a sample from a patient suffering from AML;
   contacting the patient sample with reagents specific for CD34, CD38, and CD96;
   quantitating the number of $CD34^+CD38^-CD96^+$ cells in said sample,
   wherein the number of $CD34^+CD38^-CD96^+$ cells is determined relative to the total number of $CD34^+CD38^-$ cells, and where a greater percentage of $CD34^+CD38^-CD96^+$ cells is indicative of the presence of AML stem cells, and the distribution of the AML stem cells predicts the stage of AML.

2. The method of claim 1, wherein the quantitating is performed by flow cytometry.

3. The method of claim 1, wherein the quantitating is performed by immunohistochemistry.

4. The method of claim 1, wherein the sample is a blood sample.

5. The method of claim 1, wherein the patient is undergoing treatment for AML.

6. The method according to claim 1, wherein said patient is a human.

* * * * *

UNITED STATES PATENT AND TRADEMARK OFFICE
CERTIFICATE OF CORRECTION

| | | |
|---|---|---|
| PATENT NO. | : 7,767,410 B2 | Page 1 of 1 |
| APPLICATION NO. | : 11/999809 | |
| DATED | : August 3, 2010 | |
| INVENTOR(S) | : Irving L. Weissman | |

It is certified that error appears in the above-identified patent and that said Letters Patent is hereby corrected as shown below:

In The Specification

Column 1, lines 7-9, please replace the following paragraph on page 1, beneath the title.

--GOVERNMENT RIGHTS
This invention was made with Government support under contract CA086017 awarded by The National Institutes of Health. The Government has certain rights in the invention.--

Signed and Sealed this
Twenty-sixth Day of April, 2016

Michelle K. Lee
*Director of the United States Patent and Trademark Office*